(12) United States Patent
Kosuna

(10) Patent No.: US 7,011,856 B2
(45) Date of Patent: Mar. 14, 2006

US007011856B2

(54) COMPOSITION FOR THE TREATMENT OF SYMPTOMS AND CONDITIONS ASSOCIATED WITH AGING

(75) Inventor: Ken-ichi Kosuna, Hokkaido (JP)

(73) Assignee: Amino Up Chemical Co., Ltd., Hokkaido (JP)

(*) Notice: Subject to any disclaimer, the term of this patent is extended or adjusted under 35 U.S.C. 154(b) by 173 days.

(21) Appl. No.: 10/045,972

(22) Filed: Feb. 28, 2002

(65) Prior Publication Data

US 2003/0054057 A1 Mar. 20, 2003

Related U.S. Application Data

(63) Continuation-in-part of application No. 09/591,243, filed on Jun. 9, 2000, now abandoned, which is a continuation-in-part of application No. 09/366,082, filed on Aug. 3, 1999, now abandoned.

(30) Foreign Application Priority Data

Aug. 5, 1998 (JP) .................. 10-221689

(51) Int. Cl.
*A61K 35/78* (2006.01)

(52) U.S. Cl. .............. 424/750; 424/776; 514/453; 514/456

(58) Field of Classification Search .......... 424/750, 424/776; 514/453, 456
See application file for complete search history.

(56) References Cited

U.S. PATENT DOCUMENTS 5,232,942 A * 8/1993 Imai et al.

5,554,645 A * 9/1996 Romanczyk, Jr. et al.

FOREIGN PATENT DOCUMENTS

| JP | 040237480 A | 8/1992 |
|----|----|----|
| JP | 04335879 A | 11/1992 |
| JP | 05097798 A | 4/1993 |
| JP | 07236440 A * | 9/1995 |
| WO | WO 97/36497 * | 10/1997 |

OTHER PUBLICATIONS

Durkee, Journal of Agricultural and Food Chemistry, 25 (2), 286.-7.
Registry entry 99-96-7: p-Hydroxybenzoic acid.
Snook, Nutrition, Prentice-Hall, Inc., New Jersey.
REGISTRY entry for procyanidin C2(RN No. 37064-31-6), 2001.
Teissedre et al. J. Sci. Food Agric. (1996), vol. 70, No. 1, pp. 55-61.
Trotin et al. Phytochemistry (1993), vol. 32, No. 4, pp. 929-931.
Watanabe et al. Journal of Argicultural and Food Chemistry (1997), vol. 45, No. 4, pp. 1039-1044.

* cited by examiner

*Primary Examiner*—Susan D. Coe
(74) *Attorney, Agent, or Firm*—Dennis G. Lapointe

(57) ABSTRACT

A composition including an extract of buckwheat seed and a fractionation product of the extract of buckwheat seed useful for the prevention and therapy of aging is disclosed. The composition prevents, treats and improves aging phenomena such as the symptoms of Alzheimer's syndrome and pathological lesions of the brain. Further, the composition activates and improves the function of a brain including the ability to learn, memorize, and think, as well as providing other physiological benefits.

22 Claims, 3 Drawing Sheets

COMPOSITION FOR THE TREATMENT OF SYMPTOMS AND CONDITIONS ASSOCIATED WITH AGING

This application is a continuation-in-part of application Ser. No. 09/591,243, filed Jun. 9, 2000, now abandoned, the disclosure of which is hereby incorporated by reference, which is a continuation-in-part application of application Ser. No. 09/366,082, filed Aug. 3, 1999, now abandoned. Application Ser. No. 09/366,082 claims priority under 35 U.S.C §119 from JP 10-221689 filed Aug. 5, 1998.

The present invention relates to a composition for the prevention and/or therapy of aging comprising one or more buckwheat seed components as active ingredients. More particularly, the present invention relates to a composition for the prevention and/or therapy of aging comprising an extract from buckwheat seeds, and a fraction obtained by fractionating the buckwheat seed extract.

The composition for the prevention and/or therapy of aging according to the present invention prevents and/or improves the aging phenomena, which appears in the form of various symptoms. In particular, the present invention prevents or improves brain function aging phenomena, that is: (1) prevents, treats or improves pathological lesions in the brain caused by dementia and Alzheimer's syndrome; (2) activates and improves the function of the brain's activity, including the ability to learn, the ability to memorize/think, and the ability to recognize/discern language/time and space/abstract matters, etc. In addition, the present invention inhibits in viva generation of lipid peroxides, improves hyperlipemia and diabetes, and decreases neutral fats and cholesterols, as well as performing other functions. Accordingly, the present invention is useful as a composition for the prevention and/or therapy of aging.

BACKGROUND OF THE INVENTION

The arrival of an advanced aged society causes a fear that there will be a further increase in the number of patients suffering from brain diseases such as dementia and Alzheimer's syndrome. Many people though not affected by brain diseases, experience in their daily lives such phenomena as serious forgetfulness or suffer from more frequent lapses of memory. In many cases, these phenomena would be considered a symptom of aging in the form of brain diseases.

Generally, it is believed that active oxygen species generation in living organisms participates in various disease processes. However, its relevance in brain disease has not been completely elucidated. Further, no technology has been developed that completely inhibits or controls the generation of active oxygen species. Accordingly, at present no effective and reliable preventive and therapeutic technologies exist, which are effective for the treatment and/or prevention of brain diseases.

Recently, naturally occurring plant substances having physiological activities have become the center of interest worldwide. Numerous naturally occurring plant substances have been put into practical use. Special attention has been given to buckwheat seeds, which have been used as a food source in Japan for hundreds of years. The present inventors discovered an inhibitor of lipid peroxide, a cholesterol level decreasing agent, a neutral fat levels decreasing agent and an agent for improving hyperlipemia which contains as an active ingredient an essence extracted from buckwheat husks or fractionation products thereof. A patent application directed to that invention has already been filed (Japanese Patent Application Laid-open No. Hei 10-218786).

Buckwheat is one of the most popular foods that Japanese people eat daily. In fact, buckwheat is often given to neighbors as a small house-warming gift and is a ceremonial food enjoyed on New Year's Eve. In addition, buckwheat is a popular remedy used for preventing hypertension and lowering neutral fat levels. Known components of buckwheat include, flavonoids, such as, rutin and quercetin; and polyphenols, such as, proanthocyanidine. Of these components the utilization of rutin is generally well known.

Polyphenol compounds, the secondary metabolites of plants, are well known. These compounds are present in the plant kingdom in a wide variety and in large amounts. These compounds are particularly important in the fields of pharmacy and plant chemistry since they exhibit various kinds of physiological activities. Tea polyphenols, particularly catechins, have recently become important in the field of health-care foods. These compounds are known to have various activities including, antimicrobial, antiviral, antimutational, antioxidative, anticarious, and antiallergic activities. Further, these compounds have been found to inhibit increases in blood pressure, decrease blood cholesterol levels, improve enteric bacterial flora, and exhibit deodorizing capabilities.

Research reports have been made on the components of buckwheat seed. In addition, some reports refer to the physiological activity and effect of polyphenol compounds. However, no reports have shown that buckwheat seed components have a beneficial effect in treating and improving brain function.

SUMMARY OF THE INVENTION

The present invention is directed to the prevention and/or therapy of aging phenomena. Specifically, the present invention provides a composition for the prevention and/or therapy of aging phenomena including, preventing, treating and improving the brain's pathological lesions, such as those formed by dementia and Alzheimer's syndrome. Further, the present invention activates and/or improves the function of the brain's activity including, the ability to learn, the ability to memorize/think, and the ability to recognize/discern language/time and space/abstract matters.

The present invention is also directed to efficiently collecting polyphenol compounds and other useful components contained in buckwheat seeds. It has now been found that an essence extracted from buckwheat seeds, and a fractionation/purification product obtained from the essence are useful in improving the function of the brain including the prevention and/or therapy of aging phenomena.

The composition of the present invention is also useful for inhibiting the in vivo generation of lipid peroxides, improving hyperlipemia, lowering neutral fat levels, lowering cholesterol levels, and improving diabetes. More particularly, the present invention is directed to a composition for the prevention and therapy of aging by activating a function of a brain's activity. The composition includes an active ingredient comprising a fractionation product of an aqueous extract of buckwheat seed having a molecular weight of from about 1,000 to about 10,000.

DETAILED DESCRIPTION OF THE INVENTION

Figure 1:
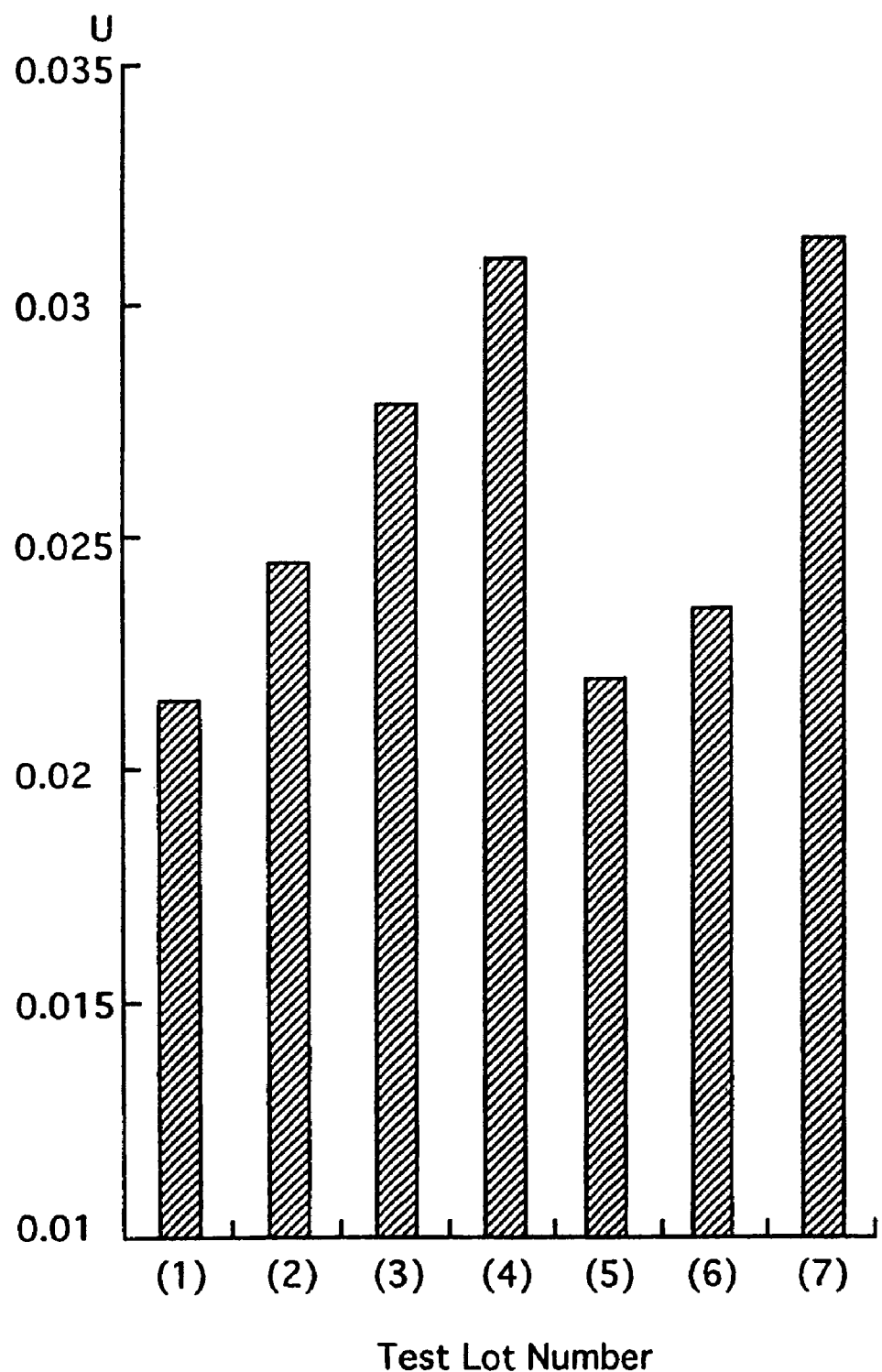
FIG. 1 is a graph illustrating the results of measurement of protein kinase C (PKC) activity in brain for various samples containing the composition of the present invention.

The present invention relates to:

1) a composition for the prevention and/or therapy of aging, comprising a component of buckwheat seed as an active ingredient;

2) a composition for the prevention and/or therapy of aging as described in 1) above, comprising an extract of buckwheat seed, or a fractionation product of the extract of buckwheat seed;

3) a composition for the prevention and/or therapy of aging as described in 2) above, comprising a fractionation product of the extract of buckwheat seed having a molecular weight of 1,000 to 10,000;

4) a composition for the prevention and/or therapy of aging as described in 2) above, comprising a fractionation product of the extract of buckwheat seed having a molecular weight of from about 1,000 to about 10,000;

5) a composition for the prevention and/or therapy of aging as described in 2) above, comprising a fractionation product of the extract of buckwheat seed having a molecular weight of about 1,500 or more;

6) a composition for the prevention and/or therapy of aging as described in any one of 1) to 5) above, which improves the function of the brain;

7) a composition for the prevention and/or therapy of aging as described in any one of 1) to 6) above, which prevents and/or improves dementia;

8) a composition for the prevention and/or therapy of aging as described in any one of 1) to 6) above, which prevents and/or improves Alzheimer's syndrome;

9) a composition for the prevention and/or therapy of aging as described in any one of 1) to 6) above, which inhibits lipid peroxide, improves hyperlipemia, lowers neutral fat levels and/or lowers cholesterol levels;

10) a composition for the prevention and/or therapy of aging as described in any one of 1) to 4) above, which activates a function of a brain's activity which prevents and treats dementia, prevents and treats Alzheimer's syndrome, inhibits lipid peroxide synthesis and/or activity; treats hyperlipemia; lowers neutral fat levels and lowers cholesterol; and 11) a composition for the prevention and/or therapy of aging as described in 5) above, which activates a function of a brain's activity which prevents and treats dementia, prevents and treats Alzheimer's syndrome, inhibits lipid peroxide synthesis and/or activity; treats hyperlipemia; lowers neutral fat levels and lowers cholesterol.

The active ingredient of the composition of the present invention, which is useful for the prevention and/or therapy of aging contains an (epi) catechin polymer having a polymerization degree of 4 to 9, and a molecular weight of from 1,000 to 10,000. The essence can be obtained by extracting buckwheat seeds with water, alcohol or other solvents, or a specified fraction obtained by further fractionating and purifying of the essence by proper means may be used in the present invention.

Generally, a buckwheat seed is a structure having a fruit portion covered with a thin membrane, i.e., a portion from which buckwheat powder is collected and an epidermis called a buckwheat husk covering it. However, in the present invention, buckwheat seed means all or any part of the structure (fruit, thin membrane, husk, etc.). In addition, these structural components may be used singly or two or more of them may be used in combination, if desired.

Buckwheat seed is properly pulverized, sieved or otherwise treated before it can be used. Before and after the pulverization and sieving, heating, pressurization or other physical treatments are performed. Apparatuses that are commonly known in the art are used in the pulverization, sieving or other treatments. These apparatuses are used under conditions known in the art.

Suitable solvents used for the extraction of an essence from buckwheat seeds usually include aqueous solvents (water, or aqueous solutions of acids, salts, bases, alcohols, etc.), organic solvents, or mixtures of these. Extraction of an essence can be performed at atmospheric pressure or under pressure at temperatures of from about room temperature to about 60° C. for about 1 to about 3 hours. If desired, the temperature may be from 70 to 150° C. and the extraction time may be shortened to 1 hour or less or extended to from about 3 to about 5 hours. In either condition, recovery of the extracted essence of a desired quality is possible. As is readily ascertainable by those skilled in the art the conditions for extraction may be properly selected depending on factors such as operability, economy and the like. After the extraction treatment, the extract is recovered by proper means, for example, by filtration or centrifugation, and if desired, various treatments may be carried out including, solvent removal, concentration of the essence component, drying, and pulverization. Proper excipients, known in the art, may be used for drying and pulverization of the concentrated extract.

Treatment of the extracted essence of buckwheat seeds by membrane treatments including, ultrafiltration or reverse osmosis or various types of chromatography give rise to recovery of targeted active fractions. Absorbents useful in the present invention include styrene/divinylbenzene base and methacrylic acid base adsorbents, hydrophilic vinyl polymer, modified dextran gel, polyacrylamide gel, reverse phase silica gel, and ion exchange resins. The absorbed fractions may be recovered by elution with hydrous alcohol, alcohol, acetone or the like. The main component of the fraction includes polyphenol compounds. In addition, several other substances having physiological activities are also present.

It is generally believed that lower molecular weight substances are absorbed more readily by living organisms. When the extracted essence of buckwheat seeds was fractionated by ultrafiltration at a molecular weight of 10,000, it was observed that fractions having a molecular weight of 10,000 or less exhibited high activity in improving the function of the brain.

The administration, to a senescence-accelerated mouse, of the composition of the present invention resulted in marked improvement in protein kinase C (PKC) activity in the brain and improved the function of brain activity including, the ability to learn, etc. Further, administration, to humans, of the composition of the present invention resulted in an improvement and increase in the ability to learn. In addition, an improvement of various states which are considered to be associated with the function of the brain, including a reduction in nervousness, dissolution of sleeplessness, and the recovery of self-possession simultaneously occurred. Further, a decrease in blood lipid peroxide levels, an increase in SOD (super oxide dismutase) activity, etc., both of which are attributable to the oxidative denaturation of substances in living organisms due to active oxygen species also occurred.

Therefore, the composition of the present invention for the prevention and/or therapy of aging prevents, treats and/or improves pathological lesion in the brain caused by diseases including as dementia and Alzheimer's syndrome. The composition of the present invention also activates and improves the function of the brain's activity, including learning, memorizing/thinking, and recognizing/discerning language/time and space/abstract matters. In addition, the composition of the present invention inhibits in vivo generation of lipid peroxides, improves SOD activity and other useful functions.

The composition of the present invention inhibits oxidative denaturation of substances in living organisms caused by active oxygen species, thereby improving hyperlipemia and diabetes, which are considered to be triggered by the generation of lipid peroxides. In addition, the composition of the present invention is useful in decreasing neutral fats, that is, lipids which are not charges in vivo, such as triacylglycerol and cholesterols. It can also stabilize and inhibit the oxidation of lipids in foods and cosmetics.

The composition of the present invention is free of both chronic and acute toxicity making it safe to use. The composition of the present invention may be administered orally or parenterally. The dosage may vary depending on age, weight, symptoms, targeted therapeutic effects and administration methods. An acceptable adult dosage is from about 100 to about 600 mg in the case of oral administration. Determining the appropriate dosage is within the skill of those skilled in the art. Generally, the composition of the present invention is administered in the form of a tablet, pill, capsule, powder, granule, syrup or the like. If desired, the composition of the present invention may also be administered in the form of an injection, a paint, or by any other means known in the art. Further, proper auxiliary materials including, starches, dextrin, sweeteners, pigments, and perfumes may be used depending upon the dosage form utilized.

BEST MODE FOR CARRYING OUT THE INVENTION

The present invention will be described particularly by referring to production examples and test examples of the composition which are useful for the prevention, therapy and/or treatment of aging. The following examples serve to provide further appreciation of the invention but are not meant in any way to restrict the scope of the invention. In the description below, % means weight % unless otherwise indicated.

PRODUCTION EXAMPLE 1

Buckwheat seeds (from Hokkaido) were washed with water, dried and the following Samples 1 to 6 were prepared.

(1) Sample 1: Whole buckwheat seeds were ground to 40 mesh or less and sieved to obtain a powder.

(2) Sample 2: 20 liters of water was added to a 1 kg portion of the powder from (1). An extraction treatment was carried out under pressure at 120° C. for 1 hour, with stirring, followed by concentrating the extracted liquid to dryness under reduced pressure to obtain an essence (yield: 264.6 g).

(3) Sample 3: 50 g of the essence from (2) was dissolved in 1 liter of water and fractionated through an ultrafiltration membrane (Advantech Ultrafilter QiQO, fractionation molecular weight:10,000) by properly adding water to obtain a portion that could not pass through the membrane (a fraction having a molecular weight of 10,000 or more), and which was then concentrated under reduced pressure to obtain a concentrate (yield: 19.8 g).

(4) Sample 4: The portion fractionated by the method described in (3) that passed through the membrane (fraction having a molecular weight of 10,000 or less) was concentrated under reduced pressure to obtain a concentrate (yield: 29.2 g). (5) Sample 5: A solution of 50 g of the essence from (2) in 100 ml of water was adsorbed by Sephadex LH-20 (Pharmacia, modified dextran gel) and then the adsorbed components were eluted with water and lyophilized to obtain a water-eluted fraction (yield: 29.4 g).

(6) Sample 6: The dextran gel-adsorbed components were eluted with an aqueous 50% acetone solution and lyophilized to obtain an acetone-eluted fraction (yield: 18.6 g).

Each of the samples obtained in Production Example 1 was measured for polyphenol content according to a Folin-Denis method. The Folin-Denis method is a method consisting of adding a Folin reagent to an aqueous solution of sample, measuring absorbance at 700 nm and obtaining the amount of polyphenol by a calibration curve using catechin. The results obtained are shown in Table 1 below.

TABLE 1

| Sample | Polyphenol Content |
|---|---|
| (1) Sample 2 (Essence extracted from buckwheat seeds) | 28.5% |
| (2) Sample 3 (Fractionated essence, molecular weight: 10,000 or more) | 24.7% |
| (3) Sample 4 (Same as above, molecular weight: 10,000 or less) | 33.6% |
| (4) Sample 5 (adsorbed in dextran gel. water-eluted portion) | 7.1% |
| (5) Sample 6 (Same as above, 50% acetone-eluted portion) | 48.2% |

TEST EXAMPLE 1

Male ddY mice at 8 weeks of age were divided into the following 7 test lots (5 animals per lot) and fed for 14 days on feeds blended with Samples 1 to 6, from Production Example 1. During the test period, the animals were allowed to take the feed and water freely. On day 15 the animals of each lot were dissected to enucleate brain and collect blood.

Test Lot (1): Control (control feed, Feed CE-2 for mouse, manufactured by Nippon Clea).

Test Lot (2): 5% of Sample 1 (buckwheat seed powder) was added to the control feed.

Test Lot (3): 0.75% of Sample 2 (extracted essence) was added to the control feed.

Test Lot (4): 0.75% of Sample 3 (fraction having a molecular weight of 10,000 or more) was added to the control feed.

Test Lot (5): 0.75% of Sample 4 (fraction having a molecular weight of less than 10,000) was added to the control feed.

Test Lot (6): 0.75% of Sample 5 (component adsorbed in gel, water-eluted portion) was added to the control feed.

Test Lot (7): 0.75% of Sample 6 (component, acetone-eluted portion adsorbed in gel) was added to the control feed.

The amount of PKC in brain, the amount of lipid peroxides and SOD activity in blood, etc. were measured by the following methods:

Method for Measuring Pkc Activity in Brain:

The sample (mouse brain) was homogenized after the addition of MPBS buffer. Following homogenization PKC activity was measured using a PKC measurement kit (Pierce Colorimetric PKC AssayKit, SpinZyme format, manufactured by PIERCE).

The results are shown in FIG. 1 (U on the vertical axis represents units). In Test Lots (2), (3), (4), and (7), i.e., test lots administered with buckwheat seed powder, essence extracted from buckwheat seeds, fractionated essence having a molecular weight of 10,000 or less, an aqueous acetone solution-eluted portion of a component of the essence adsorbed in modified dextran gel (fraction containing numerous polyphenol compounds), an increase in the amount of PKC in brain was observed as compared with the control. On the other hand, the Test Lots with the fractionated essence having a molecular weight of 10,000 or more and the water-eluted portion of a component of the essence adsorbed in modified dextran gel (fraction containing few polyphenol compounds) showed no substantial difference from the control.

TEST EXAMPLE 2

Female senescence accelerated model mice SAM-P/8 (mice showing remarkable affection in learning and memorization after 8 months from birth, attributable to defluxion of neurons) at 15 weeks of age were divided into two test lots (4 animals per lot) a control group (control feed) and buckwheat seed extracted essence group (0.5% of essence was added to the control feed), and fed for 8 weeks. During the test period, the animals were allowed to take feed and water freely.

The improvement in learning was judged by a test method using an 8-way radial maze. In this method, eight paths, partitioned with transparent walls, (observable from both the inside and the outside) are provided radially around a center. A feed is placed on the end of each path. A mouse that has been starved for 15 hours before initiation of the test is placed in the center of maze, where the entrance to each path gathers. The time is measured in which it takes the mouse to eat all the feeds placed on the ends of each path. The time it takes for entrance into wrong paths (that is, paths where the feed has already been eaten and no feed is present, the time of wrong response) is also measured. The 8-way radial maze was permanently placed in a room kept at a fixed environment and all the tests were performed therein. The tests were initiated on day 0 after the administration of samples for each test lot and then performed after a predetermined number of days. The results are shown in Tables 2 and 3.

TABLE 2

Radial 8-way maze test

| | Time for Correct Responses (Minutes) | |
|---|---|---|
| | Control | Buckwheat Seed Essence |
| Before administration | 22.04 ± 4.18 | 26.08 ± 5.22 |
| After 1 week | 4.29 ± 0.26 | 5.45 ± 0.24 |
| After 4 weeks | 3.09 ± 0.28 | 4.30 ± 2.03 |
| After 8 weeks | 4.03 ± 1.34 | 3.19 ± 0.46 |

TABLE 3

Radial 8-way maze test

| | Number of Time of Wrong Responses | |
|---|---|---|
| | Control | Buckwheat Seed Essence |
| Before administration | 62.5 ± 20.45 | 34.2 ± 11.02 |
| After 1 week | 24.5 ± 2.73 | 7.5 ± 2.80 |
| After 4 weeks | 13.7 ± 10.09 | 7.3 ± 3.71 |
| After 8 weeks | 8.0 ± 2.27 | 7.0 ± 1.99 |

As demonstrated in the radial 8-way maze tests and as is apparent from Tables 2 and 3, the time for correct response and number of wrong responses of the buckwheat seed essence group showed improvement over the control group and indicates that buckwheat seed essence has a positive effect on improving the ability to memorize.

PRODUCTION EXAMPLE 2

100 liters of water was added to 5 kg of 40 mesh or less ground product of buckwheat seeds (from Hokkaido). An extraction was performed under pressure at 150° C. for 30 minutes, with stirring. The extracted liquid was filtered and concentrated under reduced pressure to obtain a concentrate of essence, to which was added dextrin such that the solids content of the mixture was 50%. The mixture was lyophilized to obtain 2102.7 g of dry powder. This dry powder was dispensed into hard capsules in an amount of 250 mg per capsule to obtain a sample suitable for human consumption.

TEST EXAMPLE 3

Tests were performed on humans as follows: 31 healthy volunteers (11 females ages 20 to 35 years; 20 males ages 22 to 69 years) were tested by administering to each person capsules containing 250 mg of the dry powder obtained in Production Example 2 in a dosage of 4 capsules a day divided into a morning and evening dose, preferably after a meal, for 14 days. Immediately before the administration of the composition of the present invention and after completion of 14 days administration, the memorization ability of each person was tested. In addition, blood was collected for measurement of blood lipid peroxide levels and SOD activity. The test method and measurement method is as described below.

Tests on Memorization Ability (1) Memorization of Words:

Subjects were requested to memorize 27 words by pronouncing them one after another at an interval of one word every 2 seconds. Upon completion of pronouncing the entire list of words, the subjects were inactive for 3 minutes. After 3 minutes the subjects were requested to write down on a piece of paper all the words they were able to remember.

(2) Memorization of a Serial Number:

Subjects were requested to memorize a serial number having 15 digits containing an alphanumeric combination. The serial number was presented to the subjects for 15 seconds. After 15 seconds the serial number was removed and the subjects were asked to write down on a piece of paper the serial number as they remembered it.

Method for Measuring the Amount of Lipid Peroxide

A thiobarbituric acid (TBA) method was used. According to this method, phosphorus wolframate solution is added to a sample (blood) to form a precipitate (protein and lipid peroxide). The sample is then centrifuged and washed to remove similar color substances. The precipitate containing lipid peroxides together with TBA was heated under acidic conditions to obtain a red reaction product. The red reaction product was then extracted with butanol. The extract was excited with light at 515 nm, followed by measurement of the intensity of fluorescence in the vicinity of a wavelength of 553 nm. The method is also called the Yagi method or the fluorescence method.

Method for Measuring Sod Activity

The measurement of SOD activity was performed according to an NBT reduction method. Specifically, xanthine oxidase reacts with xanthine to produce a super oxide anion. The super oxide anion reduces Nitro Blue Tetrazolium to form diformazan, which is measured. If SOD or SOD-like activity is present in the sample, the formation of diformazan is decreased. Accordingly, SOD activity is obtained by defining the degree of such a decrease as an inhibition ratio.

The results of tests on the ability of memorization, measurements on blood lipid oxide levels and SOD activity are shown in Tables 4 and 5.

TABLE 4

Results of tests on memorization ability (average value of responses)

| Memorization of Words (number of memorized words) | | Memorization of Serial Number (number of correct responses) | |
|---|---|---|---|
| Before administration | 13 | Before administration | 9 |
| After administration | 18.5 | After administration | 10 |

TABLE 5

Blood lipid peroxide levels and SOD activity (average value)

| Lipid Peroxide Level (as absorbance) | | SOD Activity (unit) | |
|---|---|---|---|
| Before administration | 27 | Before administration | 11.2 |
| After administration | 23 | After administration | 12.2 |

As is apparent from the above results both the memorization of words and the memorization of a serial number were superior after administration of the composition of the present invention in comparison to the results obtained before administration. These results clearly demonstrate an improvement in memorization ability. Further support for the improvement in memorization ability is demonstrated in the blood lipid peroxide level test results. As shown in Table 5, blood lipid peroxide levels decreased after the administration of the composition of the present invention when compared to the blood lipid peroxide levels present before administration of the composition of the present invention. Likewise, SOD activity was enhanced indicating that memorization ability was increased. Therefore, these tests demonstrate that the composition of the present invention improves the function of the brain.

TEST EXAMPLE 4

Eight healthy volunteers (6 females ages 14 to 68; 2 males ages 34 and 40) were administered capsules containing 250 mg of the composition obtained in Production Example 2 at a daily dosage of 4 capsules per day comprising a morning and evening dose of 2 capsules each, for 2 months. Each person was requested to evaluate and record changes in their emotional state and feelings. For example, subjects monitored the presence, absence or changes in self-possession, peace of mind/anxiety, stress/pressure, excitation/depression, atrophy, and impatience/irritation. In addition, physical aspects were monitored, for example, the presence or absence of insomnia/sleeplessness, and headache/heavy head, etc. These results are summarized below.

Self Evaluation by Volunteers (1) Male (34 Years Old, Working in Computer Related Field)

This subject reported that he worked very hard and often felt nervous. After the initiation of taking the capsules containing the composition of the present invention he reported that his temper gradually became calmed and his ability to concentrate in all areas of his life increased.

(2) Male (40 Years Old, Quality Management Professional) Prior to taking the composition of the present invention this subject reported that he had difficulty sleeping through the night. In fact, he awoke often during the night and could not fall back asleep without listening to music. After taking the capsules containing the composition of the present invention he reported that he is able to sleep throughout the night without interruption and he slept soundly and restfully.

(3) Females (45, 51, and 58 Years Old, House Keepers) Each of these women reported that they had been suffering from insomnia for a long period of time. After taking the composition of the present invention these women reported that they were able to easily fall asleep. These women expressed relief that their insomnia had disappeared.

(4) Male (14 Years Old, Student)

This subject reported that he was irritated, agitated and nervous about his upcoming entrance examinations. He indicated that he often could not concentrate on his studies. After starting the capsules containing the composition of the present invention this subject reported he felt calm again. This subject has continued to take the composition of the present invention of his own accord.

(5) Female (21 Years Old, Unemployed)

This subject reported that for the last few years, she had been repeatedly and alternately suffering from apastia and hyperalimentosis. This caused both the subject and her parents great concern. After taking the capsules containing the composition of the present invention she reported that she gradually felt calmer and was contemplating getting her driver's license. This subjects parents also reported an improvement in this subject.

(6) Female (68 Years Old, Unemployed)

This subject reported that she often felt irritated. In addition, she reported that her judgment was very much influenced by her feelings. After taking the capsules containing the composition of the present invention she reported that she no longer felt irritated and her judgment was more balanced and her mental wellbeing had been restored.

As described above, the administration of the composition of the present invention has produced beneficial effects in humans. These beneficial effects include the acquisition and maintenance of calmness and an increased ability to concentrate, the dissolution of feelings of irritation, and the dissolution of insomnia, to name a few. These results show the beneficial effects the administration of the composition of the present invention has on the brain and nervous system of humans.

TEST EXAMPLE 5

In order to determine the physiologically active components of the present invention, the 50% acetone-eluted fraction that gave highly effective results in Test Example 1 was fractionated into (a) a fraction having a molecular weight of less than approximately 500 and (b) a fraction comprised primarily of molecules having a molecular weight of approximately 1,000 or more. The fractionation was performed on Sephadex LH-20 (Pharmacia, modified dextran gel). An experimental test was carried out on each fraction in the same manner as in Test Example 2. The results show that the latter fraction is the effective component of the composition of the present invention.

As described above and shown in Table 1, compositions of the present invention containing polyphenols, especially polymers having the structure of a polyhydric phenol compound unit are powerful agents for the prevention and/or therapy of aging. The structure of these useful composition was investigated as described below.

TEST EXAMPLE 6

50 g of the essence extracted from buckwheat was obtained in the same manner described for obtaining Sample 2 in Product Example 1. The essence was separated by MCI Gel (Mitsubishi Chemistry Co., Ltd.) using water and aqueous acetone (acetone 50%). The separated material was adsorbed on Sephadex LH-20 (Pharmacia, modified dextran gel) equilibrated with water, and fractionated with water, methanol, and 50% acetone. 6.6 g of the methanol fraction was adsorbed on Sephadex LH-20 (Pharmacia, modified dextran gel) equilibrated with ethanol, and fractionated using ethanol, aqueous ethanol (ethanol 80%, ethanol 70%, and ethanol 60%) and aqueous acetone (acetone 50%) to obtain six fractions, numbers ①~⑥. The sum total of these fractions corresponds to Sample 6 of Product Example 1 above. Generation of these 6 fractions is described below.

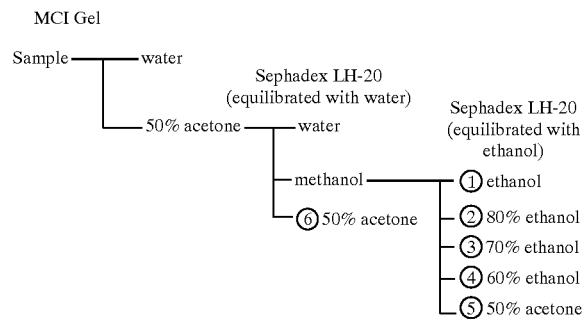

TEST EXAMPLE 7

Both the structural unit and polymerization degree of buckwheat polyphenol were examined in the thiolysis method as shown below. The principle is set forth in the following formula:

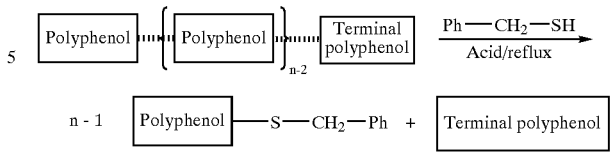

When n-mer of polyhydric phenol (unit structure) is heated and refluxed in the presence of acid (acetic acid or hydrochloric acid) and benzyl mercaptan, and bonds shown as dotted lines in the above formula are cleaved thereby, (n−1) benzylthioether units (thioether) and one terminal polyhydric phenol (non-thioether) are produced. Structural analysis of the reaction products collected in the thiolysis method reveals the unit structure of polyhydric phenol, and the polymerization degree is shown by the yield proportion of thioether and non-thioether.

Structural analysis of polyhydric phenol by the thiolysis method is described, for instance, in Y. Kashiwada et al., Ghenz P.haxm. Bul.2. 38(4) 856-860(1990). Specifically, the experiment was conducted in the following manner. The respective 100 mg dried samples of six fractions ①~⑥ obtained in Test Example 6 above were dissolved in 100 mL ethanol. 3 mL of acetic acid and 2 mL of benzyl mercaptan were added dropwise thereto. The reaction solution was then refluxed with stirring at 95° C. in nitrogen. The reaction solution was partially taken out at regular intervals of time and analyzed by HPLC under the conditions described below to determine the termination of the reaction.

```
<HPLC conditions>
Column:    TSK gel ODS-80Ts (4.6 mmID × 15 cm)
           (product of Tosoh Corp.)
Eluent:    A:0.1% acetic acid/water
           B:0.1% acetic acid/acetonitryl
               Time (min.)            % B
                0–5                    10
                5→25                  10→90
                                  (lineargradient)
               25–30                   90
Flow rate: 0.8 mL/min
Detection: 260 nm
```

Figure 2:
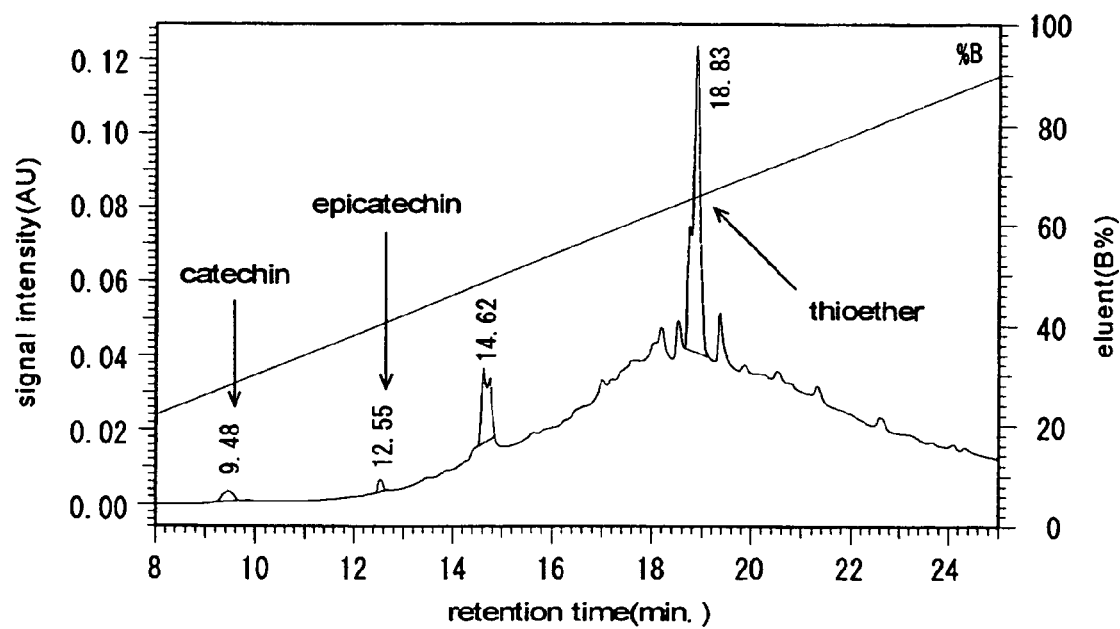
FIG. 2 is an HPLC chart of the terminal point of the thiolysis reaction of the 60% ethanol fraction described in Test Examples 6 and 7 of the composition of the present invention.

The resulting HPLC chart obtained at the terminal point of the thiolysis reaction is shown in FIG. 2. Specifically, FIG. 2 shows the results of the reaction of the 60% ethanol fraction. The peak components at retention time 9.48 min. and 12.55 min. in this figure were respectively identified as catechin and epicatechin. The approximate ratio at peak is 2:1. This result was obtained through the comparison with a standard product and further confirmed by TLC. By identification in the same manner as above, the peak components at retention time 18.89 min. was determined to comprise benzylthioether units (thioethers) of catechin and epicatechin. The content ratio is approximately 1:2. These results clearly show that polyphenol derived from buckwheat is a polymer of catechin and epicatechin. The peak component of retention time 14.62 min. is believed to be a by-product, such as an open ring compound or the like.

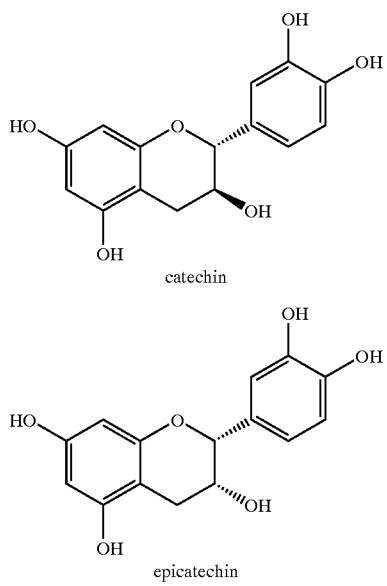

catechin epicatechin

Furthermore, from the area ratio of these peaks and the peak at the retention time 18.83 min. of the benzylthioether unit (thioether), the average polymerization degree was calculated in accordance with the following formula:

$$\text{Average polymerization degree} = \frac{A_T/I_T}{(A_C/I_C) + (A_E/I_E)} + 1$$

$A_T$: Peak area of thioether compounds
$I_T$: Molar absorption coefficient of thioether compounds
$A_C$: Peak area of catechin
$I_C$: Molar absorption coefficient of catechin
$A_E$: Peak area of epicatechin
$I_E$: Molar absorption coefficient of epicatechin The average polymerization degree of the 60% ethanol fraction in FIG. 2 is 7. In the same manner, the following result was obtained:

| | | |
|---|---|---|
| ① ethanol fraction | polyphenols (not polymerized) | |
| ② 80% ethanol fraction | average polymerization degree 3 | |
| ③ 70% ethanol fraction | average polymerization degree 5 | |
| ④ 60% ethanol fraction | average polymerization degree 7 | |
| ⑤ 50% acetone fraction (Sephadex LH-20 equilibrated by ethanol) | average polymerization degree 8 | |
| ⑥ 50% acetone fraction (Sephadex LH-20 equilibrated by water) | average polymerization degree 9 | |

Based on the above results, the polyphenol polymer isolated from the composition of the present invention is typically represented by the following structure:

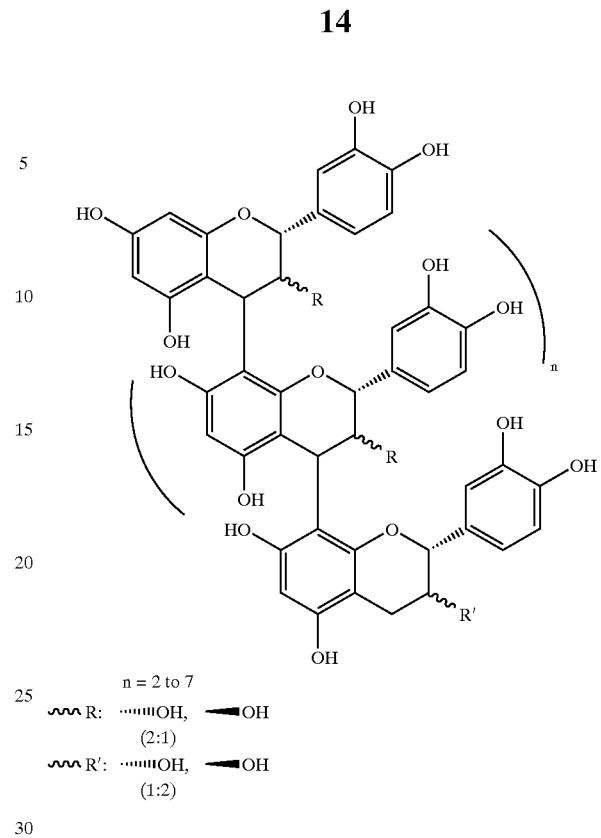

n = 2 to 7

$\sim\!\!\sim R$: ⋯⋯ⁿOH, ━OH (2:1)

$\sim\!\!\sim R'$: ⋯⋯ⁿOH, ━OH (1:2)

However, other structures with benzene rings modified by substituents are also expected.

TEST EXAMPLE 8

The anti-oxidation property of the above fractions was compared. The inhibiting activity against auto-oxidation of lipid in buckwheat polyphenol was measured in accordance with the method of Pratt et al. (*Natural Antioxidants From Plain Material, In Phenolic Compounds in Food and Their Effect on Health II: Antioxidants and Cancer Prevention*; Huang, M-T., Ho, C-T., Lee, C. Y., Eds.; American Chemical Society: Washington, DC, 1992; pp 54–71). 1 mL of 0.2 mg/mL β-carotin solution in chloroform was added to 20 mg of linoleic acid and 200 mg of Tween 20 in a shaded Erlenmeyer flask. The solution was condensed by $N_2$ gas blowing. (i) 1 mL of test sample obtained by dissolving dried samples ①~⑥ in distilled water to a concentration of 500 μg/mL and (ii) 50 mL of air-saturated distilled water prepared by introducing thereinto 0.5L of air per minute for one hour were added to the solution. The respective mixtures were incubated at 50° C. A control, containing 1 mL of distilled water instead of test sample was treated in the same manner.

In order to observe decoloration of β-carotin, the absorbance (470 nm) of the above test solutions were measured after 30 minutes and 90 minutes. The inhibiting activity was calculated by the following formula:

$$\text{Inhibiting activity against auto-oxidation of lipid} = \frac{\text{Decoloration ratio of Control} - \text{Decoloration ratio of sample}}{\text{Decoloration ratio of control}} \times 100$$

In the above formula, the decoloration ratio is a natural logarithm ln((a)/(b)) representing the proportion of the absorbance after 30 minutes (a) to the absorbance after 90 minutes (b). These results is set forth in FIG. 3.

Figure 3:
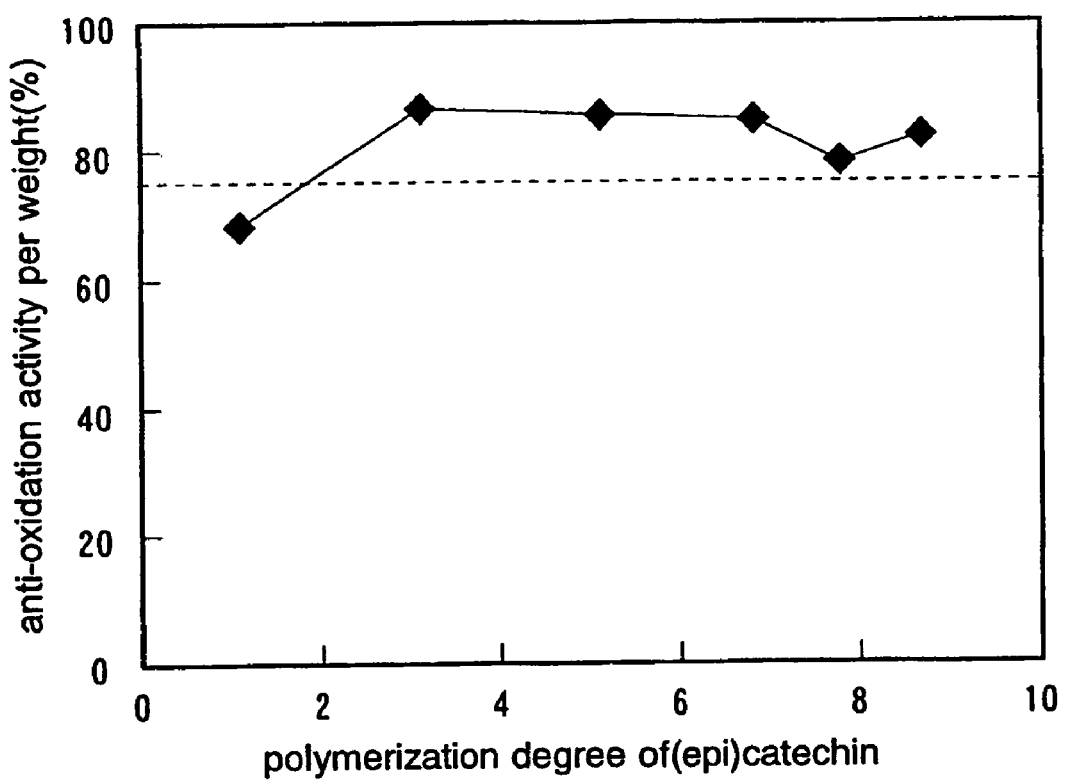
FIG. 3 is a graph illustrating the results of decoloration described in Test Example 8 of the composition of the present invention.

As shown in FIG. 3 the dashed line shows the activity value of buckwheat essence without fractionation treatment (Sample 2 in Product Example 1). Accordingly, the (epi) catechin polymer, which is the main ingredient of the buckwheat extract essence of the present invention, shows its high activity at polymerization degrees 4–7. Further, if anti-oxidation activity depended on the number of hydroxyl groups, and as long as it is based on the weight, the results for the monomer and the polymer would be the same. These experimental results, however, which show a higher activity for the polymer than the monomer reveal that the polymerization of monomer molecules provides compositions that are useful in the treatment and/or therapy of aging. Accordingly, the composition derived from buckwheat of the present invention abundantly contains polymers or oligomers of the above-mentioned polymerization degree wherein catechin and epicatechin are mixed. Further, the composition has high anti-oxidation activity.

Thus, while there has been described what are presently believed to be the preferred embodiments of the invention, those skilled in the art will understand that other and further modification can be made without departing from the spirit of the invention. It is intended that the present invention includes all such modifications as come within the true scope of the invention as set forth in the claims.

What is claimed is:

1. A composition for treating symptoms and conditions associated with aging, the composition including an active ingredient consisting essentially of:
    one of
        an aqueous extract of buckwheat seed extracted at a temperature of between 61° C. and 150° C.,
        a fractionation product of an aqueous extract of buckwheat seed, and
        a combination of said aqueous extract of buckwheat seed and said fractionation product of said aqueous extract of buckwheat seed,
    wherein the active ingredient contains polymers having 4 to 9 monomer units, said polymers having a molecular weight of from about 1,000 to about 10,000,
    wherein the composition enhances an activity of protein kinase C (PKC), improves short time memory and alleviates decrease in space cognition caused by aging.

2. The composition according to claim 1, wherein the aqueous extract of buckwheat seed has a molecular weight of about 1500 or more.

3. The composition according to claim 1, wherein the composition alleviates and treats symptoms and conditions caused by dementia.

4. The composition according to claim 2, wherein the composition alleviates and treats symptoms and conditions caused by dementia.

5. The composition according to claim 1, wherein the composition alleviates and treats symptoms and conditions caused by Alzheimer's syndrome.

6. The composition according to claim 2, wherein the composition alleviates and treats symptoms and conditions caused by Alzheimer's syndrome.

7. The composition according to claim 1, wherein the composition inhibits lipid peroxide.

8. The composition according to claim 2, wherein the composition inhibits lipid peroxide.

9. The composition according to claim 1, wherein the composition treats hyperlipemia.

10. The composition according to claim 2, wherein the composition treats hyperlipemia.

11. The composition according to claim 1, wherein the composition lowers triacylglycerol levels.

12. The composition according to claim 2, wherein the composition lowers triacylglycerol levels.

13. The composition according to claim 1, wherein the composition lowers cholesterol levels.

14. The composition according to claim 2, wherein the composition lowers cholesterol levels.

15. The composition according to claim 1, wherein the polymer having four to nine monomer units consists essentially of a catechin-epicatechin polymer having four to nine monomer units.

16. The composition according to claim 1, wherein the polymers having four to nine monomer units consist essentially of catechin-epicatechin polymers of the formula:

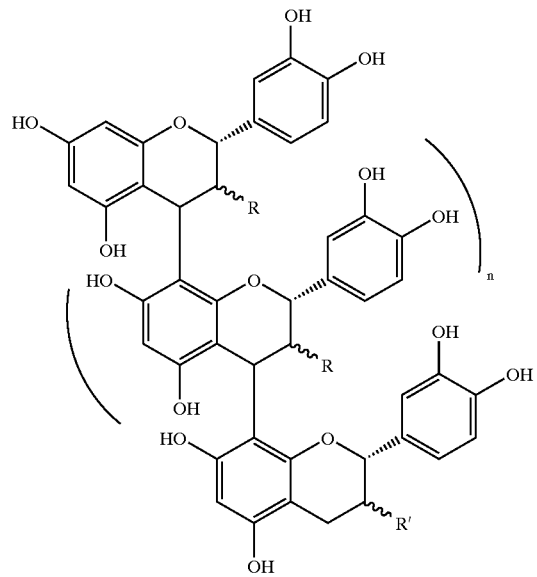

wherein a has a value of from 2 to 7, and
    R is
        ⋯ıııOH and ◂OH and the ratio of ⋯ıııOH to ◂OH is 2 to 1,
    R' is
        ⋯ıııOH and ◂OH and the ratio of ⋯ıııto ◂OH is 1 to 2 giving a ratio of catechin to epicatechin in the upper terminal and middle of 2 to 1 and a 1 to 2 ratio of catechin to epicatechin in the lower terminal.

17. The composition of claim 16 wherein n has a value of 3.

18. The composition of claim 16 wherein n has a value of 5.

19. The composition of claim 16 wherein n has a value of 7.

20. The composition of claim 2 wherein the polymer consists essentially of an catechin-epicatechin oligomer.

21. A method of improving the memory of humans and animals comprising administering to said humans and animals an effective amount of a composition having an active ingredient consisting essentially of:
    one of an aqueous extract of buckwheat seed,
a fractionation product of an aqueous extract of buckwheat seed, and
a combination of said aqueous extract of buckwheat seed and said fractionation product of said aqueous extract of buckwheat seed,
wherein the active ingredient contains polymers having 4 to 9 monomer units, said polymers having a molecular weight of from about 1,000 to about 10,000, and
wherein the polymers having 4 to 9 monomer units consist essentially of catechin-epicatechin polymers of the formula:

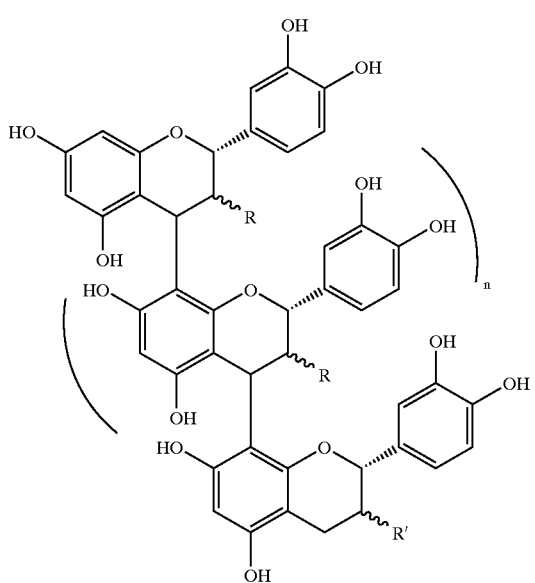

wherein n has a value of from 2 to 7, and
R is
····ıııOH and ◂━OH and the ratio of ····ıııOH to ◂━OH is 2 to 1,
R' is
····ıııOH and ◂━OH and the ratio of ····ıııOH to ◂━OH is 1 to 2 giving a ratio of catechin to epicatechin in the upper terminal and middle of 2 to 1 and a 1 to 2 ratio of catechin to epicatechin in the lower terminal wherein the composition enhances an activity of protein kinase C (PKC), improves short time memory and alleviates decrease in space cognition caused by aging.

22. A pharmaceutical product which includes as an agent, a polyphenol oligomer which is hot-water extracted from buckwheat seeds at a temperature of between 61° C. and 150° C., and contains catechin and epicatechins at a ratio of catechin to epicatechin in an upper terminal and middle of 2 to 1 and a 1 to 2 ratio of catechin to epicatechin in a lower terminal, wherein the polyphenol oligomer has 4 to 9 monomer units and said polyphenol oligomer has a molecular weight of about 1000 to about 10,000, and which enhances an activity of protein kinase C (PKC), improves short time memory and alleviates decrease in space cognition caused by aging.

* * * * *

UNITED STATES PATENT AND TRADEMARK OFFICE
CERTIFICATE OF CORRECTION

PATENT NO. : 7,011,856 B2  
APPLICATION NO. : 10/045972  
DATED : March 14, 2006  
INVENTOR(S) : Ken-ichi Kosuna It is certified that error appears in the above-identified patent and that said Letters Patent is hereby corrected as shown below:

In col. 16, lines 49-51:

Replace formula:

R' is

⫶⫶⫶⫶ OH and ▬▬ OH and the ratio of ⫶⫶⫶⫶ to to ▬▬ OH is 1 to 2 with formula:

R' is

⫶⫶⫶⫶ OH and ▬▬ OH and the ratio of ⫶⫶⫶⫶ OH to ▬▬ OH is 1 to 2

Signed and Sealed this

Eleventh Day of July, 2006

JON W. DUDAS  
*Director of the United States Patent and Trademark Office*